United States Patent [19]

Korny et al.

[11] Patent Number: 5,133,596
[45] Date of Patent: Jul. 28, 1992

[54] EYE AND HEARING PROTECTION

[75] Inventors: Lindsay M. Korny, Maughold, Isle of Man; John A. Holmes, Lancashire, United Kingdom

[73] Assignee: Hellberg International Limited, Isle of Man

[21] Appl. No.: 691,170

[22] Filed: Apr. 24, 1991

Related U.S. Application Data

[63] Continuation of Ser. No. 386,614, Jul. 31, 1989, abandoned.

[30] Foreign Application Priority Data

Aug. 2, 1988 [GB] United Kingdom ............... 8818345

[51] Int. Cl.⁵ ............................ G02C 1/00; A61F 9/00
[52] U.S. Cl. ............................................ 351/158; 2/10
[58] Field of Search ......................... 351/41, 158, 129; 2/209, 426, 15, 10, 13

[56] References Cited

U.S. PATENT DOCUMENTS 3,601,478 8/1971 Ramp ............................... 351/129 X
4,856,089 8/1989 Horton ................................... 2/209

Primary Examiner—Rodney B. Bovernick
Attorney, Agent, or Firm—Maksymonko & Slater

[57] ABSTRACT

A safety unit combining eye and hearing protection in which retention of earcups on the head of wearer is by resilience of separate side arms carrying the earcups. The resilience is resisted by a provision of a rigid frame to spectacles, or a rigid beam to goggles. Snap fitting of arms to the frame or beam enables use of the arms with either spectacles or goggles. The spectacle lens or goggle visor is separate from the rigid frame or beam.

13 Claims, 4 Drawing Sheets

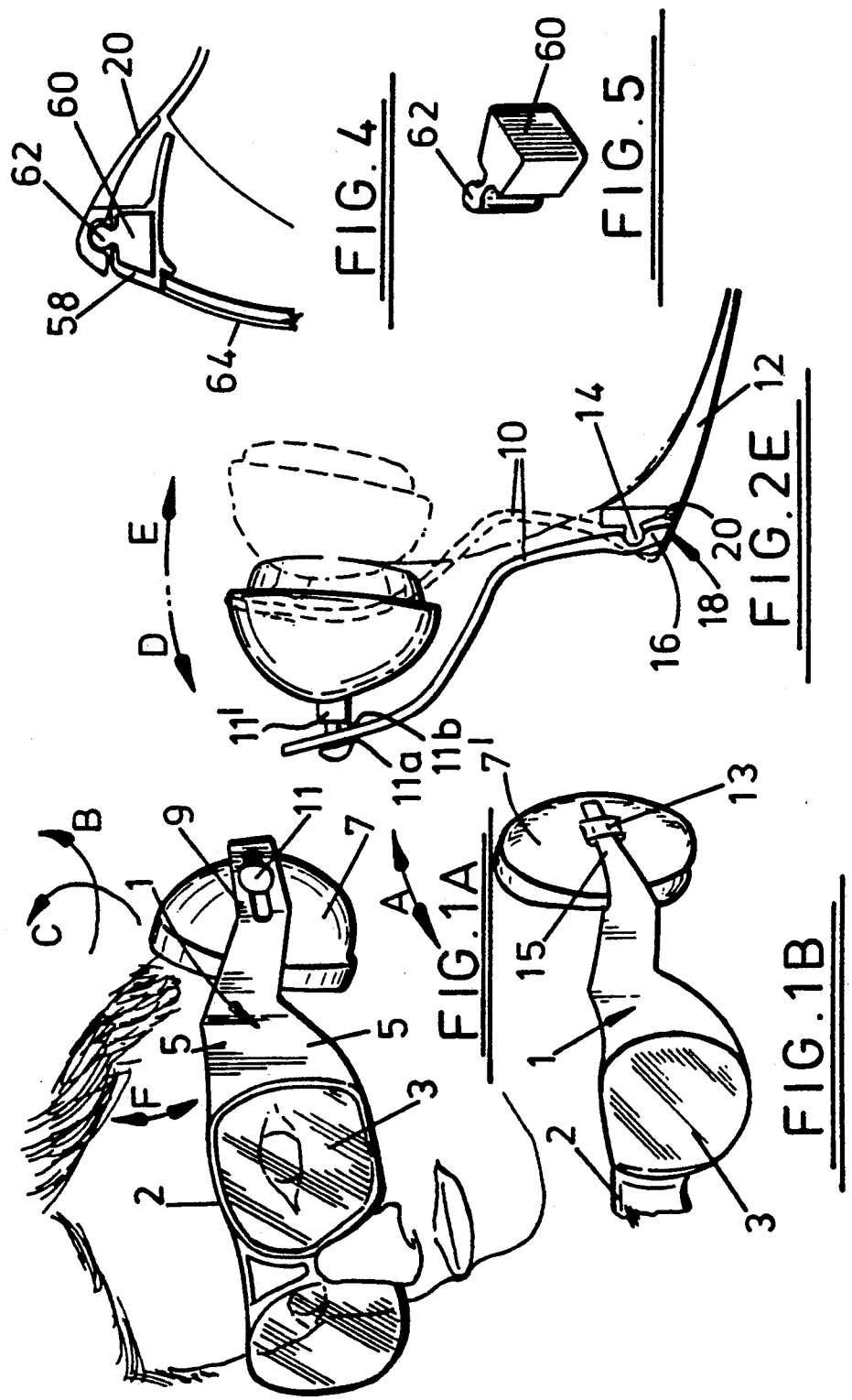

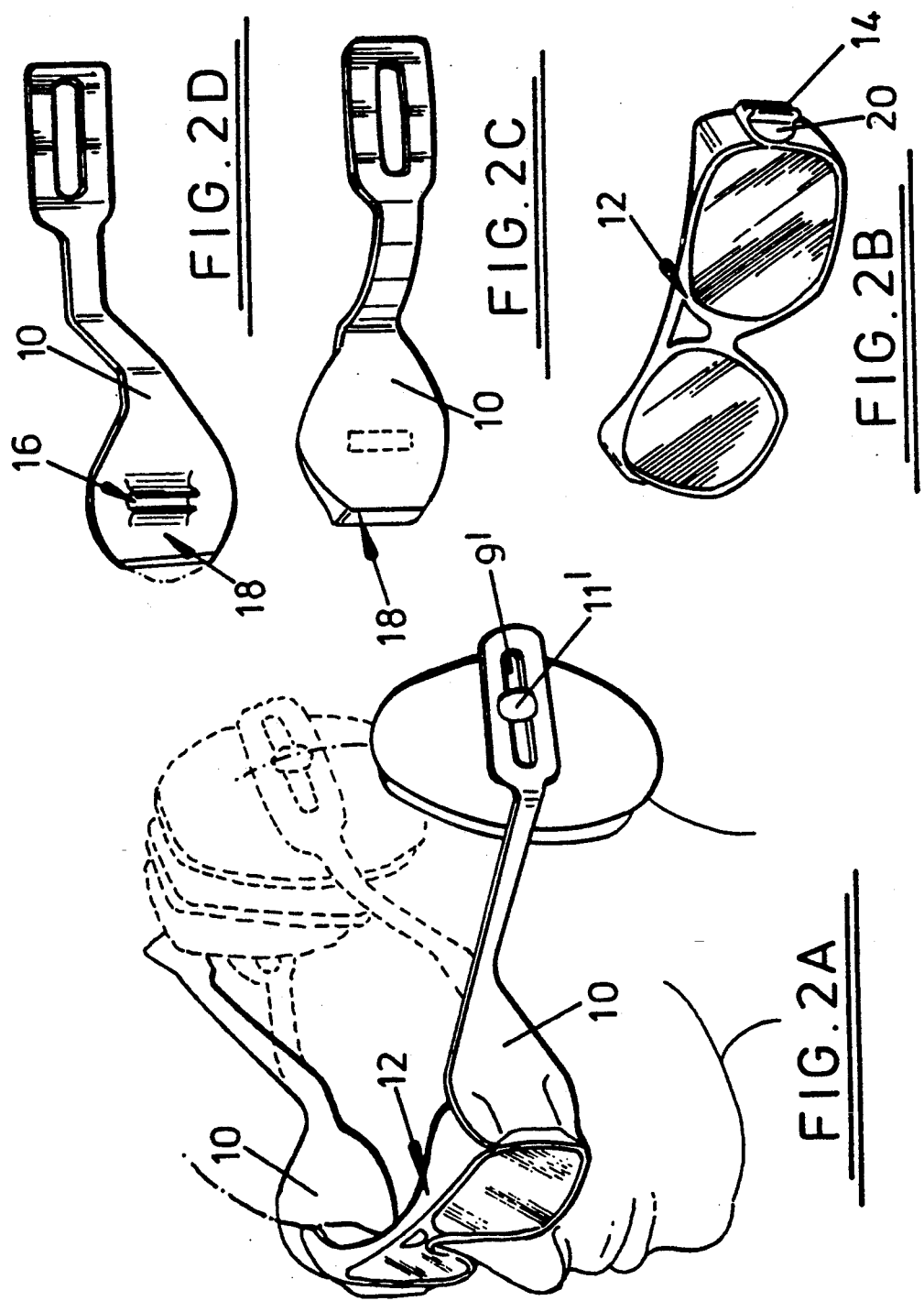

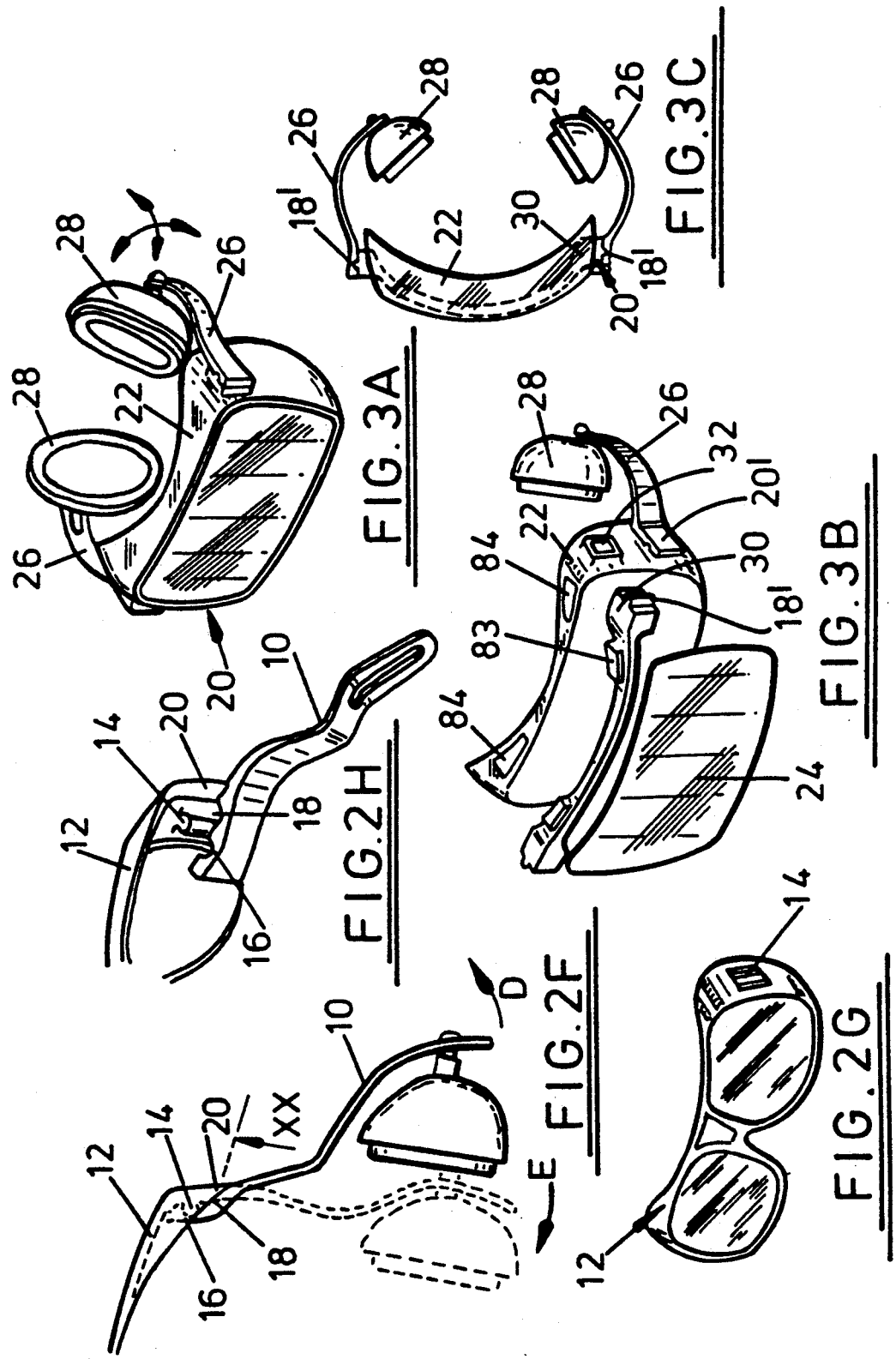

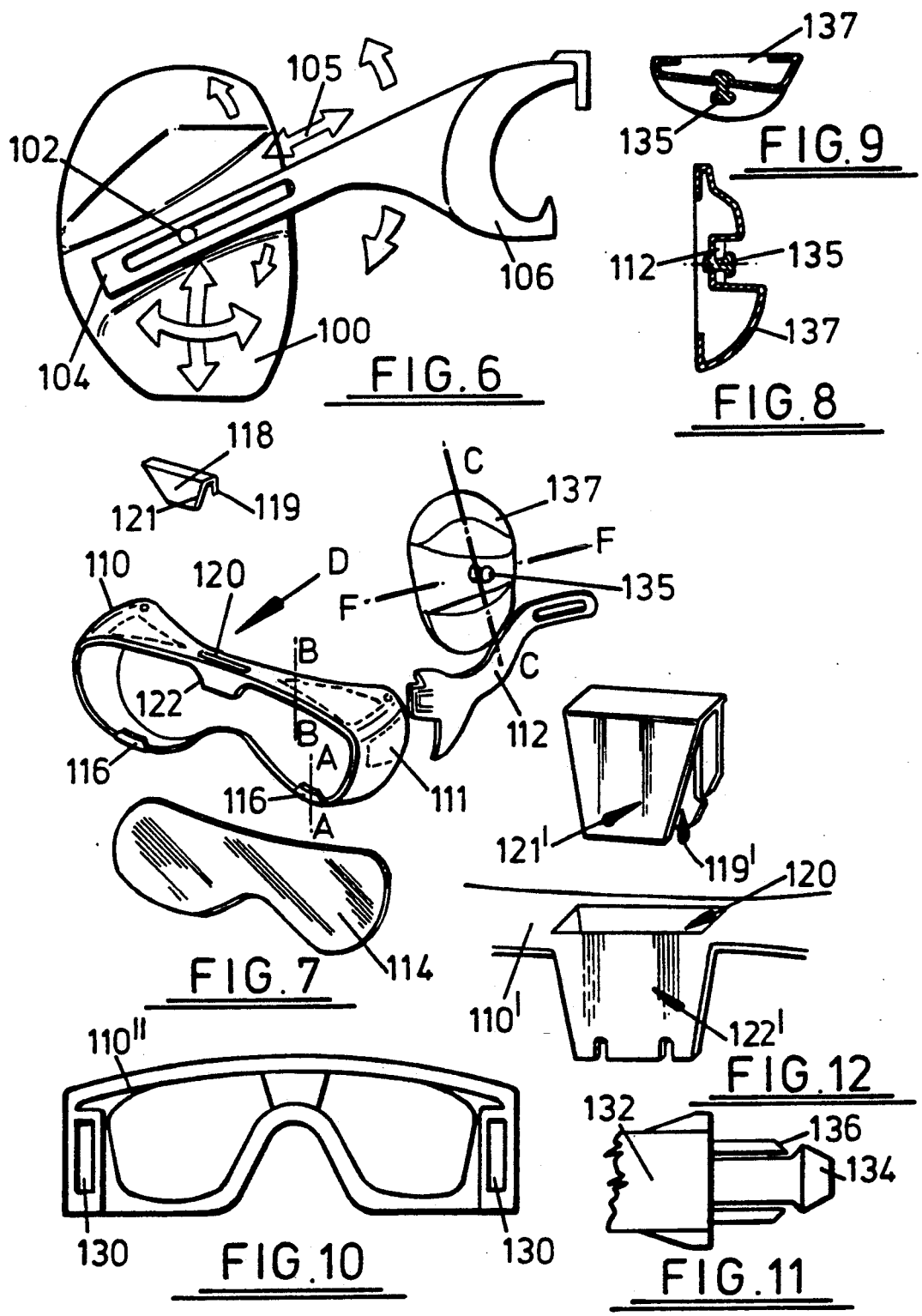

EYE AND HEARING PROTECTION

This application is a continuation of application Ser. No. 386,614, filed Jul. 31, 1989 now abandoned.

The present invention relates to a safety unit providing eye and hearing protection.

Eye protection is currently provided by one piece moulded spectacles or goggles or spectacles using replacement lenses. Visors are also known which require a headband for location purposes. To accommodate various head sizes and profiles, the spectacle side arms are adjustable in length so allowing the side arms to rest on and hook behind the ears and the front frame is pivoted with respect to the side arms. Goggles usually dispense with ear hooks in favour of an elasticated fixing passing round the head of the wearer.

Hearing protection is provided by earcups mounted on a plastic or wire headband, usually moulded in one plane. To accommodate the various head sizes and profiles the earcups are adjustable by moving along the headband, also allowing for pivoting in two planes.

To provide combined eye and hearing protection one current option is to wear separate spectacles and earmuffs. This has the disadvantage that the wearer has to tolerate both side frames and a headband which results in loss of mechanical performance of the earmuff. From the Safety Executive or Employers position, it means ensuring that the employee/operative wears two pieces of protection equipment independent of each other. Combined protection is also available by wearing a safety helmet with earmuffs on the helmet and a visor used via a helmet mounted adaptor. Often there is no need for the person to wear a safety helmet and so this combination adds unnecessary features. Another alternative is to combine earmuffs with the aforementioned face visor, but again the headband required for location purposes is often disliked by wearers, and visors in some instances are too bulky for the job.

Invariably most human faces are asymmetrical the eyes are usually not on a horizontal axis and not equidistant from the nose. Likewise the ears often vary on a horizontal plane and the distance between forehead and ear often varies on either side of the face.

There have been paper proposals for combining eye and hearing protection and in one early proposal a rigid spectacle frame has permanently hingedly connected arms incorporating spring means to bias the arms inwardly for the purpose of urging earcups carried by the ends of the arms into engagement with the head. This requires the arms to be rigid. The use of such spring means and fixedly connected arms is considered unsatisfactory and a recent paper proposal apparently aimed at overcoming problems with this earlier proposal proposes a one piece substantially U-shaped resilient and transparent frame which provides both eye protection, from a central part, and arms for the support of ear protectors mounted thereon. In our view it is technically impossible to produce a safety spectacle which meets required impact resistance safety standards and desired optical performance from a one piece resilient frame, as the resilience required to hold the ear protection in place, to give required hearing attention performance, would give rise to stress in any integral lens part which would be detrimental to optical performance.

Neither of the above paper proposals tackle the question of adjustability to cater for facial asymmetry.

The present invention aims to provide both eye and hearing protection in one unit and in a manner which is more acceptable to the wearer than present alternatives. The invention aims to provide a unit which cannot be incorrectly worn, and when fitted provides comprehensive eye and hearing protection, a major benefit. The present invention aims to provide adjustment to compensate for facial asymmetry.

Accordingly the present invention, provides a safety unit combining eye and hearing protection, comprising eye protection in the form of spectacles or goggles and hearing protection in the form of a pair of earcups/muffs, and wherein the spectacles or goggles have a pair of arm members extending therefrom which carry at their ends a respective one of the earcups.

Combining spectacles and ear muffs in this way dispenses with the need for a separate headband for the earmuffs. The spectacles/goggles rest on the bridge of the nose or otherwise, whilst the earcups/muffs fit over and/or about the ears. More particularly the earcups/muffs are held applied to the side of the head, e.g. over the ears, by tension in the arm members. This arises from elasticity (in the nature of resilience) in the arm members.

In effect the spectacle/goggles and the arm members thereof take the place of the headband of the conventional ear protector.

As flexing of the spectacle part and/or any see through safety screen or spectacle/goggle lens is undesirable, the tension has to be applied through the arm members and the means of achieving this will be described further hereinafter.

It will be understood that the unit has to be adaptable to fit various head sizes and profiles, and hence we find it convenient to have the earcup adjustably secured relative to the spectacles/goggles. This may be achieved by having the earcups mounted adjustably, say for sliding and pivoting, on the ends of the arm members or additionally or alternatively to provide an adjustable connector between the spectacles/goggles and the arm members.

According to one embodiment, facial asymmetry is compensated for by providing for both earcups to be adjustable on an inclined plane to fit ears that vary in height and distance from the forehead and to one another. Arm members linking the earcups with the spectacles/goggles provide that inclined plane. That also provides for adjustment of the frame for the spectacles/goggles in relation to the ears with pivoting therefrom to fit facial contours. Pivoting of each earcup around a respective button of the earcup or arm and cooperating with the other provides adjustment to the side elevation of the face to provide a unique fit.

We also envisage configuring the spectacle/goggle end of the arm members for securing releasably/interchangeably with different spectacle/goggle parts. These may be from different manufacturers.

In essence then, we propose a pair of arm members configured to cooperate engagingly with spectacles/goggles at one end and earcups/muffs at the other.

The present invention will now be described further hereinafter, by way of example only, with reference to the accompanying drawings, in which:

FIGS. 1a and 1b illustrate in perspective two embodiments of safety unit with different methods of attaching the ear protectors;

FIG. 2a illustrates in perspective another embodiment of safety spectacle according to the invention;

FIG. 2b is a perspective view of the spectacle frame of FIG. 2a;

FIGS. 2c and 2d illustrate respectively in perspective inside and outside views of a frame member—such as that used in the spectacles of FIG. 2a;

FIG. 2e is a plan view showing for one side connection of the arm to the spectacle frame in examplary manner;

FIG. 2f is a plan view showing for one side another embodiment of connection of the aim to the spectacle frame in examplary manner;

FIG. 2g is a perspective view of an alternative spectacle frame;

FIG. 2h is a perspective view of the embodiment of FIG. 2f with the arm disconnected;

FIG. 3a shows in perspective one embodiment of a goggle according to the invention, and FIG. 3b is an exploded perspective view of the goggle of FIG. 3a;

FIG. 3c is a plan view of the goggle of FIG. 3a;

FIG. 4 illustrates in plan an alternative connection method for attaching the arm to a goggle;

FIG. 5 is the hinge block of FIG. 4;

FIG. 6 illustrates diagrammatically the side view of a further embodiment of safety unit providing adjustment of earcup/muffs on inclined side arms;

FIG. 7 is an exploded perspective view of another embodiment showing lens retention and arms snap fitting to spectacle/goggle framing;

FIGS. 8 and 9 are sections on C—C and F—F of the earcups of FIG. 7;

FIG. 10 is a rear view of the spectacle/goggle frame showing slots for snap in arms;

FIG. 11 is a fragmentary end view of an arm showing configuration for snap in location; and FIG. 12 is an exploded fragmentary perspective view of a modified lens retention means but similar to that employed in FIG. 7.

Referring firstly to the drawing of FIG. 1a there is illustrated a safety unit having the eye protection in the form of a pair of safety spectacles having side arms 1, and a spectacle frame 2 carrying separate lenses 3 or integrally moulded lenses. The side frame is shaped to give side protection—see hatched area 5.

Material of the side arms may be transparent or opaque depending on requirements. An earcup is shown at 7 carried on an end of the side arm 1. In order to provide adjustment to suit different head sizes, the end of the side arm is provided with an elongate slot 9 in which a lug 11 projecting from the earcup is received slideably. This caters for adjustment in the direction of the arrow A. The lug also allows for rocking of the earcup relative to the side frame as represented by arrows B and C and the rocking of the spectacle frame as represented by arrow F.

The material from which the arm members are moulded has an elasticity in the nature of resilience which urges them towards a rest position with the ends of the arms and hence the earcups urged toward one another. By this means the safety unit is held in place on the wearers head.

Referring now to FIG. 1b there is illustrated one half of an alternative embodiment of safety unit having spectacles which are the same as those described with reference to FIG. 1a save for the arrangement used for coupling the side frame to the earcup 7'. Here the earcup has a slot 13 which receives slidably the end of the side arm. The arm may be recessed transverse to its length as at 15 to provide stops for ease of location of the earcup at the desired position along the length of the side arm. This may be further aided by resiliently urging the arm into contact with abutments cooperating with the recesses. The slot is preferably pivotably secured to the earcup to allow for rocking movement in the direction of arrows B and C as in FIG. 1a.

Either of the ways of connecting the side arms to the earcups as described with reference to FIGS. 1a and 1b may be employed in the following embodiments.

Referring now to FIGS. 2a to 2e, here there is illustrated an embodiment of safety unit, again having eye protection by way of spectacles, in which the arm members forming the side frames 10 are provided as separate parts to the spectacle frame 12.

The arm members 10 are preferably reversible, i.e. they can be used as left or right side frames—although this is not essential. The arm members are connected to the spectacle frame by a keying means which in the illustrated embodiment comprises a rib 14 which is part circular in cross-section and which is received in a complimentary slot 16. The arm member extends past the keying means as at 18 and is arranged to cooperate with an abutment 20 on the spectacle frame or as part of the keying means. The material of the arm members, typically a plastics or metal or a combination thereof, is chosen for properties of elasticity so that movement of the arm members in a direction of arrow D away from its rest position, generates a restoring force in the direction of arrow E—see FIG. 2E. Movement in the direction of arrow D causes the arm extension to contact the abutment 20 and thereafter will cause the arm member to bend. The dotted outline of FIGS. 2A and 2E shows the relaxed position and the solid outline the distorted portion in which the tension forces generated in the arm members are sufficient to hold the unit in place on the face and sufficiently tightly to give the required hearing attenuation.

In order to avoid distorting the spectacle frame this has to be constructed as a rigid beam.

The embodiment illustrated in FIGS. 2A to E has the type of earcup fixing as described with reference to FIG. 1a and it will be seen that the lug 11' is slidably received in the slot 9' and with provision for rocking movement by virtue of spacing of shoulders 11a, 11b.

Referring now to FIGS. 2f and 2h, here there is illustrated an embodiment of safety unit, again having eye protection by way of spectacles, in which the arm members forming the side frames 10 are provided as separate parts to the spectacle 12.

In all manners the unit works as previously described save in this unit the keying means for the arm members which in the illustrated embodiments comprises a rib 14 is moulded on the inside of spectacle 12 is part circular in cross section and is received in a complimentary slot 16. The arm member extends past the keying means as at 18 and is arranged to cooperate with an abutment 20 on the spectacle frame or as part of the keying means, the force being exerted along plane XX.

FIG. 2g shows a perspective view of spectacle 12 having the keying means 14 moulded integrally in the frame with aperturing to either side rather than as an internal or external projection.

Any hinge mechanism will perform the function of keying means 14. A projection with a spherical end and complimentary cupped reception part can provide a useful alternative also allowing for swivelling of the arm relative to spectacles.

Referring now to FIGS. 3a to 3c, here we show a safety unit in which the eye protector is in the form of goggles 20 and is provided with a pair of arm members 26, carrying at their respective ends a respective earcup 28. The arm members as with the previous embodiment of FIG. 2 utilise their elastic properties to generate the necessary location force for holding the earcups in contact with the head. Goggles traditionally have a relatively soft and flexible frame 22 for close fitting to the face of the wearer and a separate lens 24 which fits into the frame. Often the lens is more rigid than the frame. Because our arm members are subject to a bending force, this has to be resisted if it is to be sustained. Accordingly where a traditional frame construction is employed, we provide a relatively rigid beam 30 to which the arms are attached. The beam can carry a keying means similar to that described with reference to the embodiment of FIG. 2. The chief characteristic of the keying means is that it resists rotation of the arm members beyond a prescribed open position. Any non-rotatable connection will suffice where pivoting of the arm members towards a closed position does not have to be accommodated. Where it does, the arm extension and abutment which we describe with reference to FIG. 2 is preferred albeit with suitable modification to permit hinging closed.

Referring again to the embodiment of FIG. 3, it will be seen that frame 22 is apertured at 32 to receive therethrough the opposite ends of the beam 30, thus permitting the arm members 26 to be fitted into the keying means 18'. The frame is shown with a tapered sleeve moulded in the frame which prevents ingress of dirt, fluids, aerosols and in the case of welding goggles bright light. In the illustrated preferred embodiment, the lens is separate from the beam 30 and fits into the soft moulded outer frame part. Alternatively the lens may be keyed to the beam. Integral moulding is less desirable.

Where the goggles are made from a sufficiently rigid material then arm members can be attached to the goggles directly. A suitable abutment member such as that illustrated in FIG. 5 having a body 60 and rib 62 (similar to the rib 14 of FIG. 2) may be incorporated into a moulded surround 68 of the goggles 64 as illustrated in FIG. 4. The arm member 70 may then be attached. The block 60 may be affixed in any other convenient way.

A further feature of the invention is to provide the arm members with coupling means which allows them to be connected to any spectacle or goggle provided with complementary coupling means. This allows the arm members to be used with a variety of existing manufacturers spectacles or goggles. In the case of the embodiments of FIGS. 2 and 3 all that is required is for the ribbed keying means to be incorporated into the manufacturers design. Alternatively, this may be by means of a projecting tab, for fitting into a complementary slot formed in the spectacles or goggles. It will be understood that where the elasticity (resilience) of the arm member is utilised such a tab can be formed at the end of the arm member to give desired interchangeability/adaptability.

Reverting to FIG. 3b we prefer to have the rigid beam moulded with one way air ventilators 83. The goggle frame 22 is moulded with apertures 84 to receive ventilators 83.

It is envisaged that the rigid beam may incorporate resilient arm members either by providing some form of reinforcement to the beam or by virtue of using a relatively thick section.

It will be understood that the unit will be designed to meet the appropriate British Standards (currently appropriate in this regard are BS2092, BS1542 and BS679 for eye protection, and BS6344 part 1 tested to BS5108 for hearing protectors to European Standards CEN and International Standards).

Referring now to FIG. 6, an earcup/muff is illustrated at 100 having a button 102 by which it is mounted slidably in direction of arrows 105 on one of a pair of arm members 104 of the goggles/spectacles (shown at 106). The button 105 also allows for pivotal movement of the frame relative to the ears providing required adjustments (shown by arrows). It will be understood that the earcup adjustment of FIG. 1b may be employed as an alternative. The arm member is inclined downwardly from the spectacle frame and this caters for asymmetric adjustments.

Referring now to FIG. 7 there is illustrated, a spectacle frame 110 formed as a moulding with slots shown dotted 111 for receiving side arms, only one of which 112 is shown, employing resilient snap fastening—one embodiment of which is shown further with reference to FIGS. 10 and 11. We also propose a goggle in which such an arm receiving slot is incorporated in the moulded shielding thereof, but more specifically into the ends of the rigid beam thereof as of the aforedescribed keying means.

A lens is shown at 114 and is received within the frame work 110 which provides a shoulder against which the lens abuts around its periphery, with tabs 116 to provide lowermost retention effectively providing a U-shaped slot on section A—A with the section elsewhere such as B—B being generally L-shaped to provide a lip surrounding the periphery of the lens and the aforesaid abutment surface. Location is achieved by a generally U-shaped clip 118 one leg 119 of which is received (e.g. snap fittingly) in an opening 120 in the frame and the other 121 serves to trap the lens between it and a flange 122 of the frame 110 i.e. the lens is held against the outer face of flange 122.

FIG. 12 illustrates an alternative embodiment of lens retention clip essentially the same as that of FIG. 14 wherein one limb has spring legs 119' engaging in the opening 120' with the lens being trapped between the leg 121' and the outer face of flange 122' of the frame 110. The above lens retention methods are also possible for a goggle.

Referring to FIGS. 10 and 11—here a spectacle frame 110'' (although it could be applied to a goggle) has rear slots 130 to receive the end of a respective arm 132 which end provides resilient tab 134 and side guides 136 (either as part of or separate limbs of the tab 134) to provide interconnection in a snap fitting manner. The end 134 when pushed home cooperates with a groove, slot, recess or shoulder at the end of slot 130 for retention purposes, but facilitating removal by deformation of the end against its inherent resilience otherwise locating the arm member with respect to the frame part. The aforementioned tab construction is particularly advantageous in construction permitting selection of arms and frames (e.g. spectacles or goggles) for assembly together from a variety of different designs. The arm 112 of FIG. 7 is slotted to receive button 135 of the earcup 137. That cup is recessed to receive the arm as shown in FIGS. 8 and 9 allowing for inclined slidable adjustment. The alternative is a fitting as per FIG. 1b. As with the previously described embodiments, the arm 112 or 132 is resilient to provide required head gripping.

It is also envisaged to provide optional preferably hinged side arms of traditional ear location type adapted to fit to the spectacle frames in place of the earcup carrying arm members, to facilitate use of the spectacles without earcups when required. Goggles may have slots to receive the traditional elastic headband when the earcup carrying arm members are removed.

We claim:

1. A unitary construction of safety unit combining eye and hearing protection comprising means for protecting eyes and means for protecting hearing, said eye protecting means being selected from the group consisting of a goggle and a spectacle, each one including a frame means and at least one lens affixed thereto, the frame means including integrated reinforcement means whereby said reinforced frame means remains substantially rigid and without substantial deformation during normal use of the safety unit; the hearing protection means including a pair of earcups; a pair of arm members adapted to cooperate with and extend from the respective opposed temple regions of the reinforced frame means by way of mutually complimentary engageable coupling means of releasable snap-fit type, which coupling means are disposed at one end of the respective arm members and at laterally spaced positions of the reinforced frame means, which arm members carry at their ends a respective one of the earcups and where the arm members resiliently react against the substantially rigid frame means to hold the earcups to the side of a wearer's head in use and which receive the earcups in a manner to provide adjustability on an inclined plane to account for facial asymmetry, the mounting of the lens being isolated from the resilience of the arms by the provision of the frame reinforcement means.

2. A safety unit according to claim 1 wherein the arm members are separate from the frame means.

3. A safety unit according to claim 2 comprising keying means which serves to connect the arm means releasably with the frame means.

4. A safety unit according to claim 3 in which the keying means is constructed as a releasable snap-in connection.

5. A safety unit according to claim 4 wherein the releasable snap-in connection comprises a spigot part carrying a resilient abutment and a mating opening in which it is received and having a shoulder with which the resilient abutment engages when inserted to retain in position.

6. A safety unit according to claim 1 in which the arm means are inclined downwardly from the frame means and receive the earcups adjustably to account for facial asymmetric.

7. A safety unit according to claim 1 in which the frame means is apertured to receive the lenses which are retained by abutment means of the frame means and a releasable retention clip which is engagable with the frame means and the lenses.

8. The safety unit of claim 1 in which the reinforcement means is a separate beam member operatively affixed to the frame means whereby flexure of the frame means is substantially eliminated during normal use and wear of the safety unit.

9. A safety unit according to claim 1 in which the beam member carries a goggle like face shield.

10. A safety unit according to claim 9 wherein the beam member incorporates ventilation openings.

11. The safety unit of claim 8 in which the arm members are operatively affixed to the beam member whereby the safety unit is retained on a wearer's head through the flexure of the arm members while the frame means remains substantially rigid and not deformed.

12. The safety unit of claim 1 in which the arm members are releasably detachable from the reinforced frame means.

13. A safety unit combining eye and hearing protection comprising means for protecting eyes and means for protecting hearing, said eye protecting means including a frame means and at least one lens affixed thereto, the frame means including integral reinforcement means whereby said reinforced frame means remains substantially rigid and without substantial deformation during normal use of the safety unit, a pair of arm members adapted to cooperate with and extend from the respective opposed temple end regions of the reinforced frame means; the hearing protection means including a pair of earcups in integral cooperation with the eye protecting means, each earcup being carried at one end of a respective arm member whereby the eye and hearing protecting means define a unitary safety unit construction in which the eye protection means further defines earcup positioning and biasing means and in which the hearing protection means and arm members further define means affixed to said opposed end regions of the frame means for positioning and retaining the eye protecting means whereby the frame means defines means both for retaining said lens and for retaining and positioning said ear protecting means whereby a hearing protection means is provided without inclusion of a separate headband member.

* * * * *